US007626164B2

(12) United States Patent
Yoon et al.

(10) Patent No.: US 7,626,164 B2
(45) Date of Patent: Dec. 1, 2009

(54) METHOD OF SCANNING A SUBSTRATE, AND METHOD AND APPARATUS FOR ANALYZING CRYSTAL CHARACTERISTICS

(75) Inventors: Young-Jee Yoon, Gyeonggi-do (KR); Jung-Taek Lim, Gyeonggi-do (KR); Tae-Sung Kim, Gyeonggi-do (KR); Chung-Sam Jun, Gyeonggi-do (KR); Sung-Hong Park, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 226 days.

(21) Appl. No.: 11/564,726

(22) Filed: Nov. 29, 2006

(65) Prior Publication Data
US 2007/0120054 A1    May 31, 2007

(30) Foreign Application Priority Data
Nov. 29, 2005    (KR) .................. 10-2005-0114836

(51) Int. Cl.
*G01N 23/00*    (2006.01)
(52) U.S. Cl. .................. 250/310; 250/306; 250/307; 250/311
(58) Field of Classification Search .............. 250/306, 250/307, 310, 311; 438/14; 324/751
See application file for complete search history.

(56) References Cited

U.S. PATENT DOCUMENTS

| | | | | |
|---|---|---|---|---|
| 5,466,934 | A | * | 11/1995 | Adams et al. ............... 250/307 |
| 5,654,548 | A | * | 8/1997 | Fink et al. .................. 250/311 |
| 5,892,224 | A | * | 4/1999 | Nakasuji ..................... 250/310 |
| 6,091,249 | A | * | 7/2000 | Talbot et al. ................ 324/751 |
| 6,913,939 | B2 | * | 7/2005 | Kang .......................... 438/16 |

(Continued)

FOREIGN PATENT DOCUMENTS

JP    2001-053122    2/2001

(Continued)

OTHER PUBLICATIONS

English language abstract for Korean Publication No. 2004-0065592.

(Continued)

*Primary Examiner*—David A Vanore
*Assistant Examiner*—Michael Maskell
(74) *Attorney, Agent, or Firm*—Harness, Dickey & Pierce (57) ABSTRACT

In an embodiment, a method of scanning a substrate, and a method and an apparatus for analyzing crystal characteristics are disclosed. A sequential scan on the scan areas using a first electron beam and a second electron beam are repeatedly performed. The electrons accumulated in the scan areas by the first electron beam are removed from the scan areas by the second electron beam. When a size of the scan area is substantially the same as a spot size of the first electron beam, adjacent scan areas partially overlap each other. When each of the scan areas is larger than a spot size of the first electron beam, the adjacent scan areas do not overlap each other. Images of the scan areas are generated using back-scattered electrons emitted from each of the scan areas by irradiating the first electron beam to analyze crystal characteristics of circuit patterns on the substrate.

19 Claims, 6 Drawing Sheets

U.S. PATENT DOCUMENTS

| | | | |
|---|---|---|---|
| 7,126,357 B2 * | 10/2006 | Kang | 324/751 |
| 7,211,796 B2 * | 5/2007 | Nagahama et al. | 250/310 |
| 7,217,924 B1 * | 5/2007 | Mankos et al. | 250/310 |
| 2004/0000642 A1 * | 1/2004 | Veneklasen et al. | 250/311 |
| 2004/0161866 A1 * | 8/2004 | Kang | 438/16 |
| 2005/0176159 A1 * | 8/2005 | Kang | 438/14 |

FOREIGN PATENT DOCUMENTS

| | | |
|---|---|---|
| JP | 2005-156516 | 6/2005 |
| KR | 10-0272124 | 8/2003 |
| KR | 2004-0065592 | 7/2004 |

OTHER PUBLICATIONS

English language abstract for Japanese Publication No. 2001-053122.

English language abstract for Japanese Publication No. 2005-156516.

* cited by examiner

METHOD OF SCANNING A SUBSTRATE, AND METHOD AND APPARATUS FOR ANALYZING CRYSTAL CHARACTERISTICS

CROSS-REFERENCE TO RELATED APPLICATIONS

This application claims priority to Korean Patent Application No. 2005-114836 filed on Nov. 29, 2005, the contents of which are herein incorporated by reference in their entirety for all purposes.

BACKGROUND

1. Field of the Invention

The present invention relates to a method of scanning a substrate, and a method and an apparatus for analyzing crystal characteristics. More particularly, the present invention relates to a method of scanning a substrate using an electron beam, and a method and an apparatus for analyzing crystal characteristics.

2. Description of the Related Art

Generally, semiconductor devices are manufactured by repeatedly performing a deposition process, a chemical and mechanical polishing (CMP) process, a photolithography process, an etching process, an implanting process, a cleaning process, an inspecting process, and so on. Due to design rule reductions of the semiconductor devices, circuit patterns of the semiconductor devices have also been reduced to a size similar to that of a typical crystal of a material included in the circuit patterns. Characteristics of the material, such as physical characteristics, electric characteristics, surface characteristics, and internal characteristics, are influenced by crystal characteristics having a nano-scale in a range of a few nanometers to several tens of nanometers. In addition, the above-described crystal characteristics need to be adjusted while manufacturing the semiconductor devices.

An electron beam has been widely used for analyzing crystal characteristics. A conventional method of analyzing crystal characteristics may begin with irradiating an electron beam onto an analysis region of a substrate. This will instantly charge the analysis region of the substrate with electrons. Some electrons are then elastically collided with atomic nuclei in the analysis region and discharged and scattered out from a surface of the analysis region of the substrate.

Hereinafter, a scattered electron resulting from this elastic collision between irradiating electrons and target atomic nuclei is referred to as a back-scattered electron.

Back-scattered electrons are detected by an analysis device. A diffraction pattern, for example a diffraction spectrum, is obtained on a basis of the detected back-scattered electrons. The crystal characteristics are analyzed by using the diffraction pattern. U.S. Pat. No. 5,466,934 (issued to Brent, et al.) discloses just such a conventional method and an apparatus for detecting crystal defects by using back-scattered electrons.

Although an analysis device using the diffraction pattern has a resolution degree inferior to that of a transmission electron microscope, the above analysis technology using the diffraction pattern has some advantages. In particular, a specimen is not required for analyzing the substrate and a larger surface of the substrate is analyzed compared with the analysis using the transmission electron microscope. In addition, the above analysis technology using the diffraction pattern facilitates a quantification of analysis results compared with the analysis using the transmission electron microscope.

However, diffraction patterns may not be used for analyzing the crystal characteristics in a circuit pattern of which a size is in a range from a few nanometers to several tens of nanometers. Further, the above analysis technology using the diffraction pattern may not be used for analyzing the crystal characteristics in a composite circuit pattern such as an insulator due to an electric effect caused by the electron beam.

Accordingly, alternate methods and devices are necessary to address these limitations in the prior art.

SUMMARY

An example embodiment provides a method of scanning a substrate that has nano-scaled circuit patterns.

Another example embodiment provides a method of analyzing crystal characteristics in the above nano-scaled circuit patterns using the above scanning method.

Still another example embodiment provides an apparatus for analyzing crystal characteristics in the above nano-scaled circuit patterns using the above scanning method.

According to one aspect of the embodiments, there is provided a method of scanning a substrate. In the above method, a first electron beam is irradiated onto a first scan area of the substrate for scanning the first scan area. A second electron beam is irradiated onto the first scan area of the substrate, so that the electrons accumulated in the first scan area by the first electron beam are removed from the first scan area by the second electron beam. The first electron beam is irradiated onto a second scan area of the substrate for scanning the second scan area. The second electron beam is irradiated onto the second scan area of the substrate, so that the electrons accumulated in the second scan area by the first electron beam are removed from the second scan area by the second electron beam. A sequential irradiation of the first and second electron beams is repeatedly performed onto rest of the scan areas of the substrate.

In an example embodiment, the first and second areas of the substrate have a size larger than a spot size of the first electron beam and are adjacent to each other.

In an example embodiment, the first and second areas of the substrate have a size that is substantially identical to a spot size of the first electron beam and partially overlap each other.

In an example embodiment, the first electron beam includes a pulse.

According to another aspect, there is provided a method of analyzing crystal characteristics of a circuit pattern on a substrate. In the above method, a plurality of scan areas is set up on a substrate. A sequential scanning is repeatedly performed on the scan areas using a first electron beam and a second electron beam, so that the electrons accumulated in the scan areas by the first electron beam are removed by the second electron beam. Diffraction patterns are generated at each of the scan areas using back-scattered electrons emitted from each of the scan areas by irradiating the first electron beam. The crystals of a circuit pattern on the substrate are analyzed using the diffraction patterns to analyze the crystal characteristics of the circuit pattern.

In an example embodiment, each of the scan areas has a size larger than a spot size of the first electron beam and does not overlap neighboring scan areas.

In an example embodiment, the scan areas have substantially the same size as a spot size of the first electron beam, and each of the scan areas partially overlaps neighboring scan areas.

In an example embodiment, the first electron beam includes a pulse.

According to another aspect, there is provided an apparatus for analyzing crystal characteristics. The apparatus includes a stage, a first beam source, a second beam source, a first detector, a first image generator, a first image processor, a second detector, a second image generator and a second image processor. The stage supports a substrate, and the first beam source irradiates a first electron beam to the substrate. The first electron beam includes a pulse irradiating at a slope with respect to the substrate. The second beam source irradiates a second electron beam to the substrate, so that electrons accumulated in the substrate by the first electron beam are removed from the substrate. The first detector detects secondary electrons emitting from the substrate by irradiating the first electron beam, and the first image generator generates circuit pattern images of the substrate using the detected secondary electrons. The first image processor defines an analysis region on the substrate using the circuit pattern images. The second detector detects back-scattered electrons emitting from the substrate by irradiating the first electron beam, and the second image generator generates diffraction pattern images using the detected back-scattered electrons. The second image processor analyzes the crystal characteristics of the circuit pattern using the diffraction pattern images.

According to the embodiments, the first electron beam is irradiated in a pulse form so that a reduced amount of charge is accumulated in a substrate. Further, a second electron beam removes the accumulated electrons by the first electron beam from the substrate. As a result, crystal characteristics of the circuit pattern on the substrate are easily analyzed without noises due to the accumulated electrons even though the circuit pattern has become much finer.

BRIEF DESCRIPTION OF THE DRAWINGS

Example embodiments of the invention will become readily apparent by reference to the following detailed description when considering in conjunction with the accompanying drawings. In the drawings.

DESCRIPTION OF THE EMBODIMENTS

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the present invention are described herein with reference to cross-sectional illustrations that are schematic illustrations of idealized embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments, providing a method of scanning of a substrate and a method and an apparatus for analyzing crystal characteristics, will be described more fully with reference to the accompanying drawings in which example embodiments of the present invention are shown.

Figure 1:
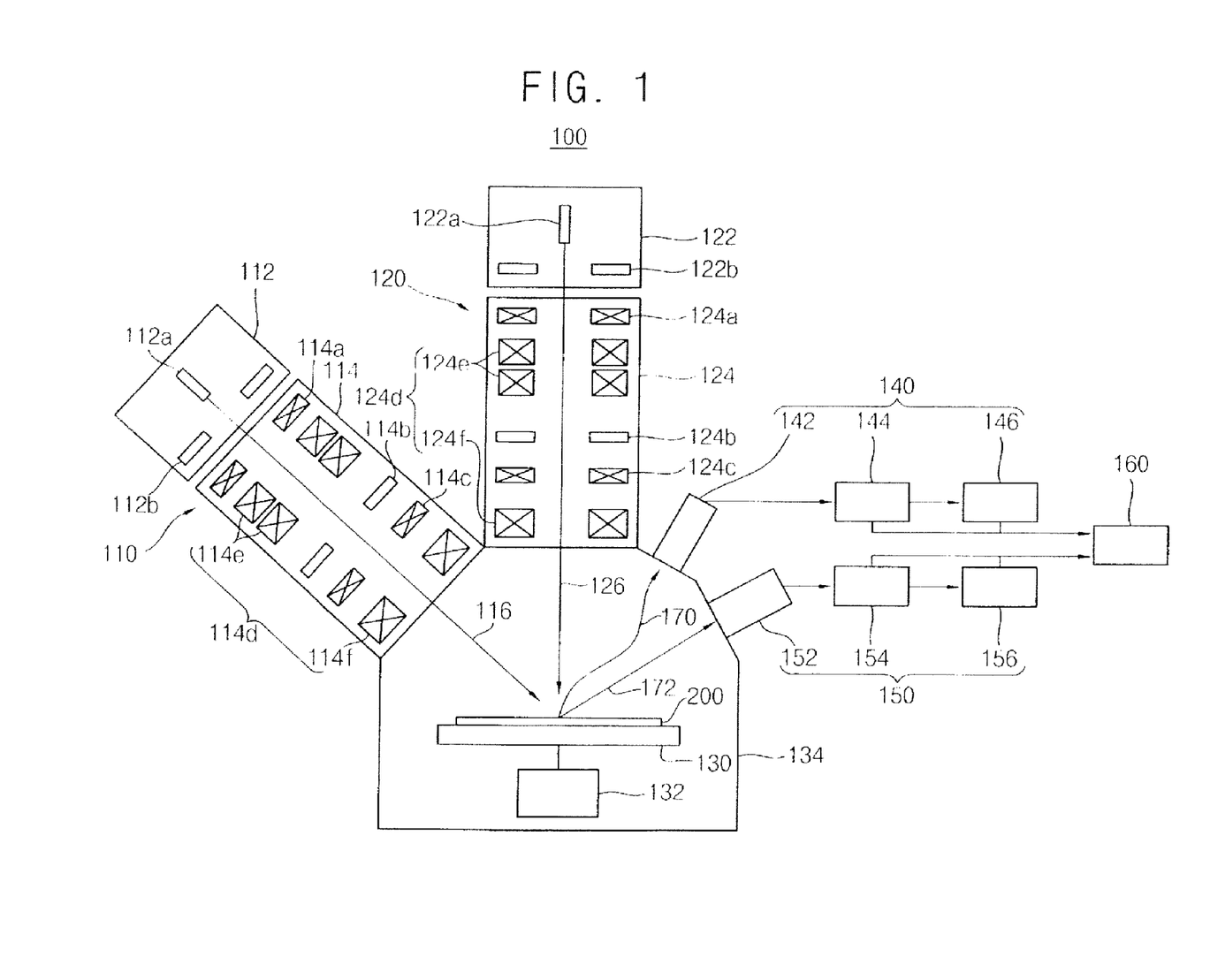
FIG. 1 is a view illustrating an apparatus for analyzing crystal characteristics of a substrate in accordance with an example embodiment.

Apparatus for Analyzing Crystal Characteristics FIG. 1 is a view illustrating an apparatus for analyzing crystal characteristics in accordance with an example embodiment of the present invention.

Referring to FIG. 1, the apparatus 100 for analyzing the crystal characteristics includes a first beam source 110 for generating a first electron beam 116, a second beam source 120 for generating a second electron beam 126, a stage 130 for supporting a substrate 200, a setting unit 140 for setting an analysis region on the substrate 200, an analysis unit 150 for analyzing the crystal characteristics in the analysis region on the substrate 200, and a display unit 160 for displaying the analyzed crystal characteristics.

The first beam source 110 includes a first electron gun 112 and a first column 114. The first electron gun 112 generates electrons, and the electrons are formed into the first electron beam 116 in the first column 114. Then, the first electron beam 116 may be irradiated from the first column 114 onto a surface of the substrate 200 such as a silicon wafer. The first electron gun 112 has a filament 112a for generating the electrons and an extraction electrode 112b for extracting the electrons. The first column 114 has a magnetic lens 114d, an alignment coil 114a, a diaphragm 114b, and a scanning coil 114c.

In an example embodiment, the magnetic lens 114d may be an electromagnet having a cylindrical body and a coil wound along a surface of the body. A magnetic field may be generated around the electromagnet, and the electrons passing though the magnetic lens 114d may be condensed into a beam line due to an electromagnetic alignment effect, to thereby form the first electron beam 116. For example, the electrons generated by the first electron gun 112 may be condensed into a cross-sectional area of about 10 μm to about 50 μm from the area of about 10 nm to about 50 nm by the magnetic lens 114d.

The magnetic lens 114d has a pair of condensing lenses 114e, and an objective lens 114f. The pair of condensing lenses 114e may condense the electrons generated from the first electron gun 112 and control an intensity of the first electron beam 116. A focal distance of an objective lens 114f is adjusted so that a focus of the first electron beam 116 is condensed onto a surface of the substrate 200.

The alignment coil 114a is positioned between the extraction electrode 112b and the magnetic lens 114d, and aligns the electrons passing though the extraction electrode 112b along a central axis of the magnetic lens 114d.

The diaphragm 114b and the scanning coil 114c are positioned between the pair of condensing lenses 114e and the objective lens 114f. The scanning coil 114c may control a path of the first electron beam 116 to scan across the substrate 200.

In an example embodiment, the first electron beam 116 includes a pulse. That is, the first electron beam 116 is discontinuously irradiated onto the substrate 200 from the first beam source 110 in a pulse form, so that a significantly reduced amount of charge is accumulated in the substrate 200 compared to when the first electron beam 116 is continuously irradiated onto the substrate 200. As a result, a subsequent electron beam is much less influenced by the electrons accumulated in the substrate 200 by a former first electron beam.

The first beam source 110 irradiates the first electron beam 116 at a slope with respect to a surface of the substrate 200. For example, the slope of the first electron beam 116 with respect to the substrate 200 is an angle of rotation in a range from about 20° to about 30° from the surface of the substrate 200.

The second beam source 120 includes a second electron gun 122 and a second column 124. The second electron gun 122 generates electrons for the second electron beam 126. The second column 124 transforms the electrons generated in the second electron gun 122 into the second electron beam 126, and irradiates the second electron beam 126 onto the surface of the substrate 200.

The second electron gun 122 has a filament 122a for generating the electrons and an extraction electrode 122b for extracting the electrons. The second column 124 has a magnetic lens 124d, an alignment coil 124a, a diaphragm 124b, and a scanning coil 124c.

The magnetic lens 124d comprises a pair of condensing lenses 124e, and an objective lens 124f.

The second beam source 120 is substantially identical to the first beam source 120. Thus, a detailed description of the second beam source 120 is omitted hereinafter.

In an example embodiment, the second beam source 120 irradiates the second electron beam 126 perpendicularly to the surface of the substrate 200. The second electron beam 126 discharges the substrate 200 of charges accumulated by the first electron beam 116.

In an example embodiment, the second beam source 120 irradiates the second electron beam 126 with a charge polarity that is opposite to that of the charge accumulated in the substrate 200. The charge of the substrate 200 and the charge of the second electron beam 126 neutralize each other so that the substrate 200 is discharged by the second electron beam 126.

In another example embodiment, the second beam source 120 irradiates the second electron beam 126 with a charge polarity that is the same as that of the charge accumulated in the substrate 200. The charge of the substrate 200 and the charge of the second electron beam 126 collide with each other, so that the substrate 200 is discharged by the second electron beam 126.

The second electron beam 126 may be a continuous wave or a discontinuous wave, e.g., a pulse.

The stage 130 supports the substrate 200, and a driving section 132 is connected to the stage 130. The driving section 132 controls the stage 130 so that the first electron beam 116 and the second electron beam 126 are irradiated onto an entire surface or a portion of the surface of the substrate 200. In an example embodiment, the driving section 132 includes a driving robot that is operated in accordance with a rectangular coordinate system.

A chamber 134 holds the stage 130, and a portion of the chamber 134 is connected to a vacuum generator (not shown). An inside of the chamber 134 may be maintained under a vacuum condition by the vacuum generator while analyzing the crystal characteristics, thereby preventing the first and second electron beams 116 and 126 from colliding with any gas molecules in the chamber 134. As a result, paths of the first and second electron beams 116 and 126 are not altered until reaching the substrate 200.

The setting unit 140 defines a region on the substrate 200 on which the analysis process is performed. The setting unit 140 includes a first detector 142, a first image generator 144 and a first image processor 146.

When the first electron beam 116 is irradiated on the substrate 200, some electrons inelastically collide with electrons and scatter from a surface of the substrate 200. Hereinafter, the electrons inelastically scattered from the surface of the substrate 200 will be referred to as the secondary electrons.

The first detector 142 detects secondary electrons 170 emitted from the substrate 200 by the first electron beam 116, and generates an electric current corresponding to the detected secondary electrons 170. The first detector 142 also converts the electric current into a voltage corresponding thereto, and the corresponding voltage is sufficiently amplified in the first detector 142. In an example embodiment, a bias voltage is applied to the first detector 142, thereby detecting the secondary electrons 170.

The first image generator 144 is electrically connected to the first detector 142, and generates image information on a circuit pattern of the substrate 200 in accordance with the amplified voltage. In an example embodiment, the image information includes a plurality of gray levels in each pixel corresponding to the circuit pattern of the substrate 200, so that the first image generator 144 includes an analog-to-digital (AD) converter for generating a digital signal, e.g., the gray levels, from an analog signal, e.g., the amplified voltage.

The first image processor 146 is electrically connected to the first image generator 144. In addition, the first image processor 146 defines an analysis region in which defects in the crystals are detected from the image information on the circuit patterns. For example, the analysis region includes an active region on the substrate 200.

The analysis unit 150 analyzes the crystal characteristics forming the circuit patterns on the substrate 200. The analysis unit 150 includes a second detector 152, a second image generator 154 and a second image processor 156.

When the first electron beam 116 is irradiated on the substrate 200, some electrons are elastically collided with an atomic nucleus and scattered from a surface of the analysis region on the substrate. Elastically scattered electrons are referred to as the back-scattered electrons.

The second detector 152 detects back-scattered electrons 172 emitted from the substrate 200 by the first electron beam 116, and generates an electric current corresponding to the detected back-scattered electrons 172. This situation arises, for example, when the first electron beam 116 is irradiated onto the analysis region of the substrate 200.

The second detector 152 may also convert the electric current into a voltage, and the corresponding voltage may be sufficiently amplified in the second detector 152. In an example embodiment, a bias voltage is applied to the second detector 152, thereby detecting the back-scattered electron 172.

The second image generator 154 is electrically connected to the second detector 152, and generates image information in accordance with the amplified voltage. The image information may show diffraction patterns of the back-scattered electrons 172.

The second image processor 156 may be electrically connected to the second image generator 154. In addition, the second image processor 156 may analyze crystal orientations of the circuit patterns using the diffraction patterns of the image information. The crystal characteristics may be analyzed using the crystal orientations.

The display unit 160 is electrically connected to each of the first image generator 144, the first image processor 146, the second image generator 154 and the second image processor, respectively. The display unit 160 may display the image information on the circuit pattern of the substrate 200 that is acquired from the first image generator 144 and the analysis region defined by the first image processor 146. Further, the display unit 160 may display the diffraction patterns of the analysis region generated by the second image generator 154 and an analysis result generated by the second image processor 156.

In the apparatus 100 used to analyze the crystal characteristics in the present embodiment, the first electron beam 116 is irradiated in a pulsed manner to decrease an amount of charge generated by the beam. After the second electron beam 126 discharges the accumulated electrons that are charged by the first electron beam 116, the first electron beam 116 is irradiated again thereby preventing the influence of the accumulated electrons. Because the crystals of the circuit patterns have a nano-scale in a range of a few nanometers to several tens of nanometers, the crystal characteristics may be easily and clearly analyzed.

Method of Scanning a Substrate

FIGS. 2A to 2D are plan views illustrating a method of scanning a substrate in accordance with an example embodiment.

Figure 2A:
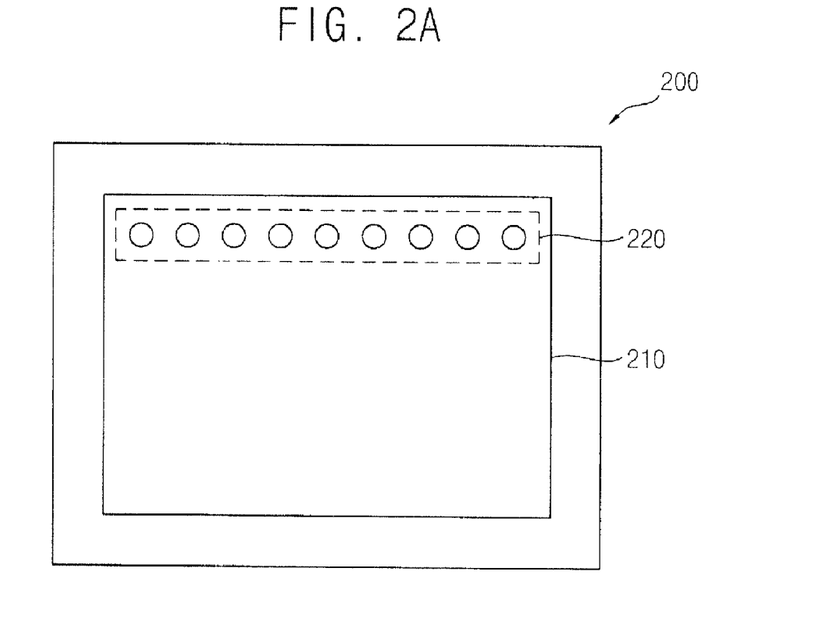
FIGS. 2A to 2D are plan views illustrating a method of scanning a substrate in accordance with an example embodiment.

Referring to FIGS. 1 and 2A, the first electron beam 116 is irradiated onto an analysis region 210 of the substrate 200, thereby scanning a first scan area 220 in the analysis region 210 of the substrate 200. The first scan area 220 has a line shape, and, in this embodiment, a size of the scan area 220 is greater than a spot size of the first electron beam 116. In an example embodiment, the first electron beam 116 is irradiated onto the substrate 200 at an angle. The beam may be in a discontinuous form such as a pulse at a slope with respect to the substrate 200. For example, the first electron beam 116 may be irradiated at an angle ranging from about 20° to about 30° with respect to a surface of the substrate 200.

The pulsed first electron beam 116 is discontinuously irradiated onto the scan area 220 from the first beam source 110 so that a greatly reduced amount of charge is accumulated in the scan area 220 compared to when the first electron beam 116 is not pulsed, e.g., continuously irradiated onto the scan area 230.

The spot size of the first electron beam 116 may be larger than that of the first electron beam 116 at a higher resolution.

Figure 2B:
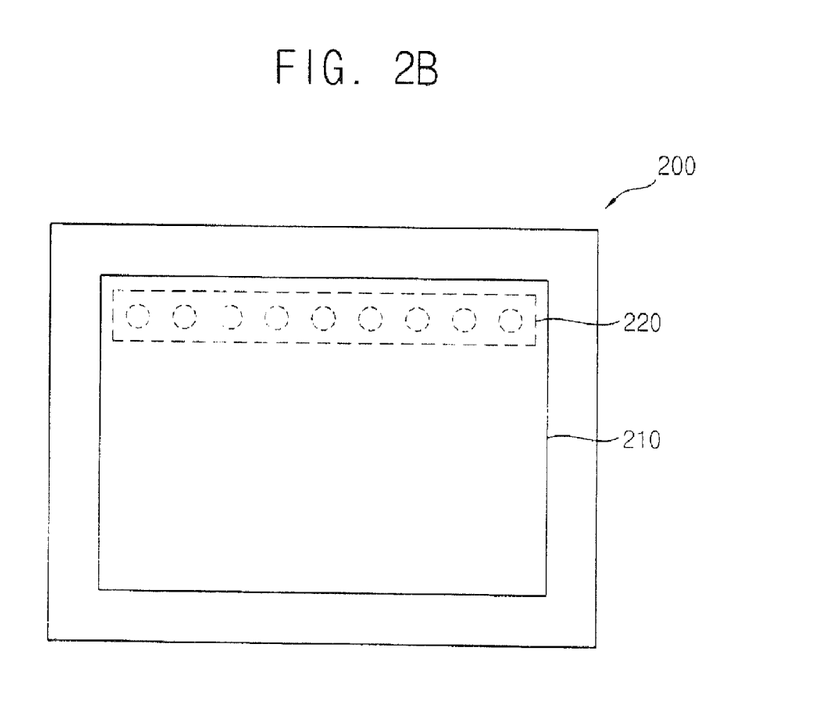

Referring to FIG. 2B, the second electron beam 126 is irradiated onto the analysis region 210, thereby scanning the first scan area 220 in the analysis region 210. A spot size of the second electron beam 126 may be substantially the same as the spot size of the first electron beam 116. In an example embodiment, the second beam source 120 irradiates the second electron beam 126 so that it has a charge polarity opposite to that of the charge accumulated in the first scan region 220. The charge of the first scan region 220 and the charge of the second electron beam 126 are neutralized by each other, so that the first scan region 220 is discharged by the second electron beam 126. In another example embodiment, the second beam source 120 irradiates the second electron beam 126 so that it has a charge polarity that is the same as that of the charge accumulated in the first scan region 220. The charge of the first scan region 220 and the charge of the second electron beam 126 collide with each other, so that the first scan region 220 is discharged by the second electron beam 126.

Accordingly, the second electron beam 126 discharges the first scan region 220 in which the charge is accumulated by the first electron beam 116. The second electron beam 126 may be a continuous or pulsed wave. Further, the second electron beam 126 may be incident at an oblique angle or perpendicular with respect to the substrate 200.

Figure 2C:
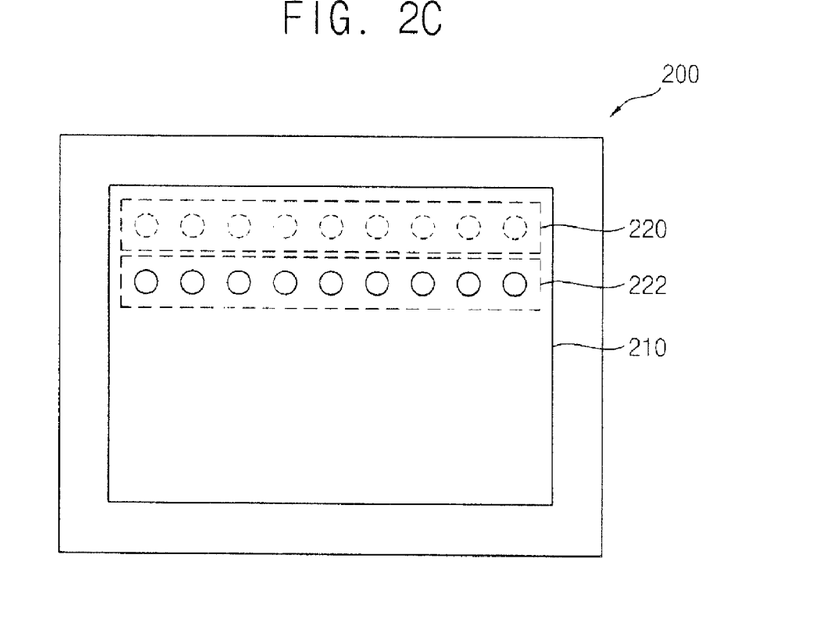

Referring to FIG. 2C, after moving the substrate 200, the first electron beam 116 is irradiated onto an analysis region 210 of the substrate 200, thereby scanning a second scan area 222 in the analysis region 210 of the substrate 200. The second scan area 222 may be adjacent to the first scan area 220 without overlapping with the first scan area 220. The second scan area 222 also may have a line-shape. A size of the second scan area 222 may be greater than the spot size of the first electron beam 116. In an example embodiment, the first electron beam 116 is pulsed at an angle with respect to the substrate 200. For example, the first electron beam 116 is irradiated at an angle ranging from about 20° to about 30° with respect to a surface of the substrate 200.

Figure 2D:
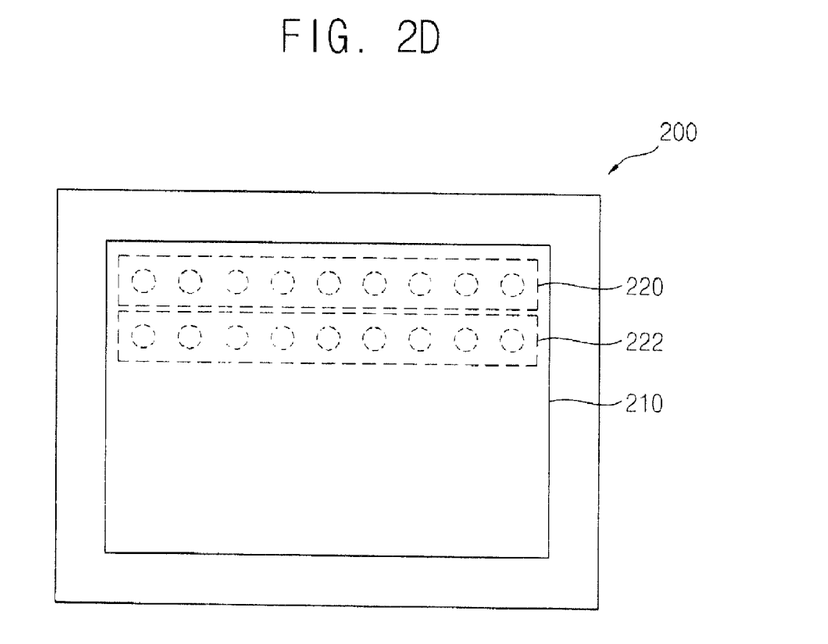

Referring to FIG. 2D, the second electron beam 126 is irradiated onto the analysis region 210, thereby scanning the second scan area 222 in the analysis region 210. The spot size of the second electron beam 126 may be substantially the same as the spot size of the first electron beam 116. In an example embodiment, the second beam source 120 irradiates the second electron beam 126 having a charge polarity opposite to that of the charge accumulated in the second scan region 222. The charge of the second scan region 222 and the charge of the second electron beam 126 neutralize each other, so that the second scan region 222 is discharged by the second electron beam 126. In another example embodiment, the second beam source 120 irradiates the second electron beam 126 having a charge polarity that is the same as that of the charge accumulated in the second scan region 222. The charge of the second scan region 222 and the charge of the second electron beam 126 collide with each other, so that the second scan region 222 is discharged by the second electron beam 126. Accordingly, the second electron beam 126 discharges the second scan region 222 in which the charge is accumulated by the first electron beam 116. The second electron beam 126 may be a continuous wave or pulsed. Further, the second electron beam 126 is irradiated at an angle or perpendicularly with respect to the substrate 200.

In addition, a sequential irradiation of the first and second electron beams 116 and 126 may be repeatedly performed on a subsequent scan area on the rest of the analysis region. Each of the scan areas may be closely adjacent to neighboring scan areas, but not overlapping.

According to the present embodiment, the first electron beam 116 is irradiated in a pulse form to decrease an amount of accumulated electrons. After the second electron beam 126 discharges the electrons accumulated by the first electron beam 116, the first electron beam 116 is irradiated again onto the substrate 200, thereby preventing the influence of the accumulated electrons. As a result, in an example embodiment of the present invention, the accumulated electrons do not cause any noise.

The following describes a method of scanning a substrate in accordance with another example embodiment.

FIGS. 3A to 3D are plan views illustrating a method of scanning a substrate in accordance with another example embodiment.

Figure 3A:
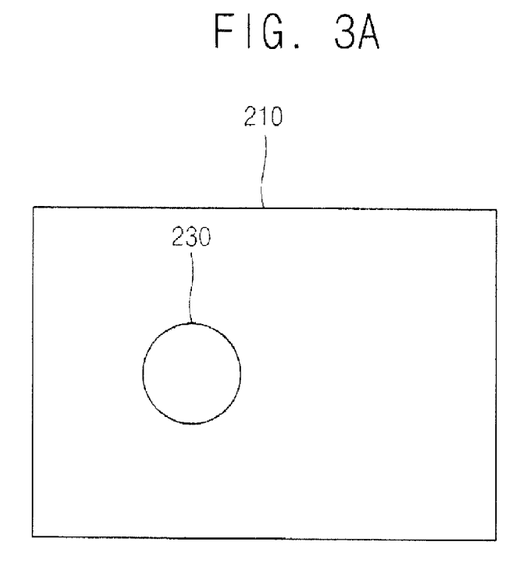
FIGS. 3A to 3D are plan views illustrating a method of scanning a substrate in accordance with another example embodiment.

Referring to FIG. 3A, a first electron beam 116 is irradiated onto a first scan area 230 in the analysis region 210 of the substrate 200. A spot size of the first electron beam 116 may be substantially the same as a size of the first scan area 230. In an example embodiment, the first electron beam 116 is pulsed at a slope with respect to the substrate 200. For example, the first electron beam 116 is irradiated at an angle ranging from about 20° to about 30° with respect to a surface of the substrate 200.

The first electron beam 116 is irradiated onto the first scan area 230 from the first beam source 110 in a pulsed manner, so that a greatly reduced amount of electrons is accumulated in the first scan area 230 compared to when the first electron beam 116 is continuously irradiated onto the first scan area 230. The spot size of the first electron beam 116 may be smaller than the spot size of the first electron beam 116 at a lower resolution.

Figure 3B:
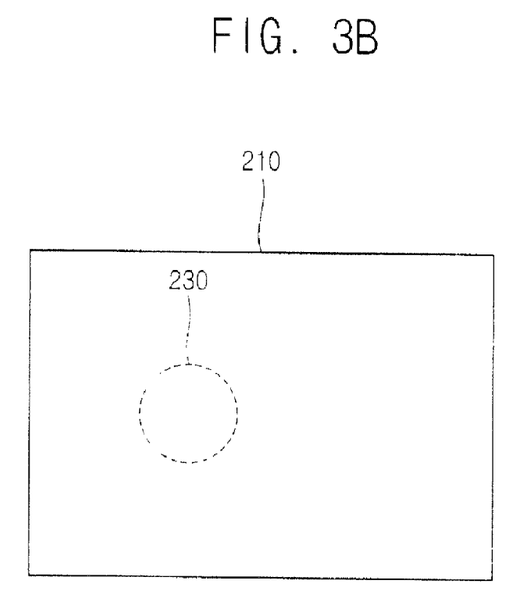

Referring to FIG. 3B, a second electron beam 126 is irradiated onto the first scan area 230 of the analysis region 210. A spot size of the second electron beam 126 is also substantially the same as the size of the first scan area 230. In an example embodiment, the second beam source 120 irradiates the second electron beam 126 having a charge polarity opposite to that of the charge accumulated in the first scan region 230. The charge of the first scan region 230 and the charge of the second electron beam 126 neutralize each other, so that the first scan region 230 is discharged by the second electron beam 126. In another example embodiment, the second beam source 120 irradiates the second electron beam 126 having a charge polarity that is the same as that of the charge accumulated in the first scan region 230. The charge of the first scan region 230 and the charge of the second electron beam 126 collide with each other, so that the first scan region 230 is discharged by the second electron beam 126. Accordingly, the second electron beam 126 discharges the first scan region 230 in which the charge is accumulated by the first electron beam 116. The second electron beam 126 may be a continuous wave or a pulse. Further, the second electron beam 126 is irradiated at an angle or perpendicularly with respect to the substrate 200.

Figure 3C:
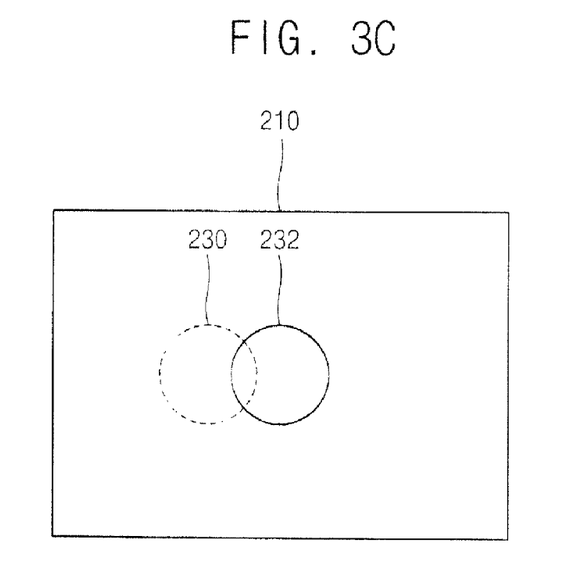

Referring to FIG. 3C, after moving the substrate 200, the first electron beam 116 may be irradiated onto a second scan area 232 in the analysis region 210 of the substrate 200. The second scan area 232 may partially overlap the first scan area 230. A spot size of the first electron beam 116 may be substantially the same as a size of the second scan area 232. In an example embodiment, the first electron beam 116 is irradiated in a pulse form at a slope with respect to the substrate 200. For example, the first electron beam 116 is irradiated at an angle ranging from about 20° to about 30° with respect to a surface of the substrate 200.

Figure 3D:
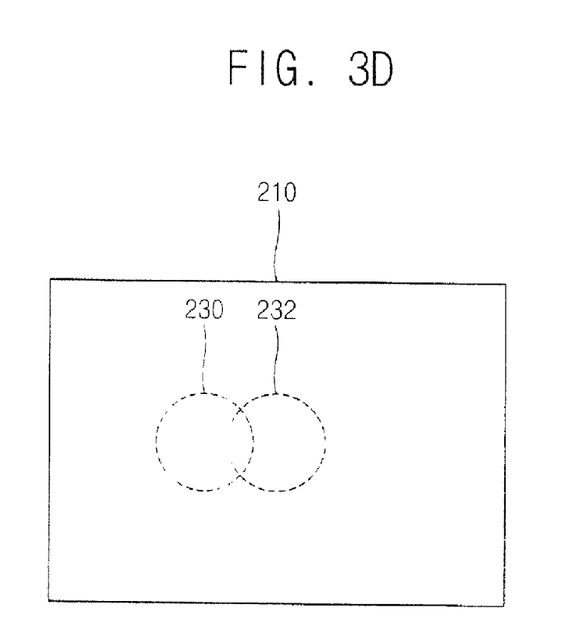

Referring to FIG. 3D, the second electron beam 126 may be irradiated onto the second scan area 232 of the analysis region 210. The spot size of the second electron beam 126 may also be substantially the same as the size of the second scan area 232. In an example embodiment, the second beam source 120 irradiates the second electron beam 126 having a charge polarity opposite to that of the charge accumulated in the second scan region 232. The charge of the second scan region 232 and the charge of the second electron beam 126 neutralize each other, so that the second scan region 232 is discharged by the second electron beam 126. In another example embodiment, the second beam source 120 irradiates the second electron beam 126 having a charge polarity that is the same as that of the charge accumulated in the second scan region 232. The charge of the second scan region 232 and the charge of the second electron beam 126 collide with each other, so that the second scan region 232 is discharged by the second electron beam 126. Accordingly, the second electron beam 126 discharges the second scan region 232 in which the charge is accumulated by the first electron beam 116. The second electron beam 126 may be a continuous wave or a pulse. Further, the second electron beam 126 is irradiated at an angle or perpendicularly with respect to the substrate 200.

In addition, a sequential irradiation of the first and second electron beams 116 and 126 may be repeatedly performed on a subsequent scan area on the rest of the analysis region. Each of the scan areas may partially overlap the neighboring scan areas.

According to the present embodiment, the first electron beam 116 is irradiated in a pulse form to decrease an amount of accumulated electrons generated by the first electron beam 116. After the second electron beam 126 discharges the accumulated electrons generated by the first electron beam 116, the first electron beam 116 is irradiated again onto the substrate 200, thereby preventing the influence of the accumulated electrons. As a result, the accumulated electrons do not cause any noise.

Method of Analyzing Crystal Characteristics

Figure 4:
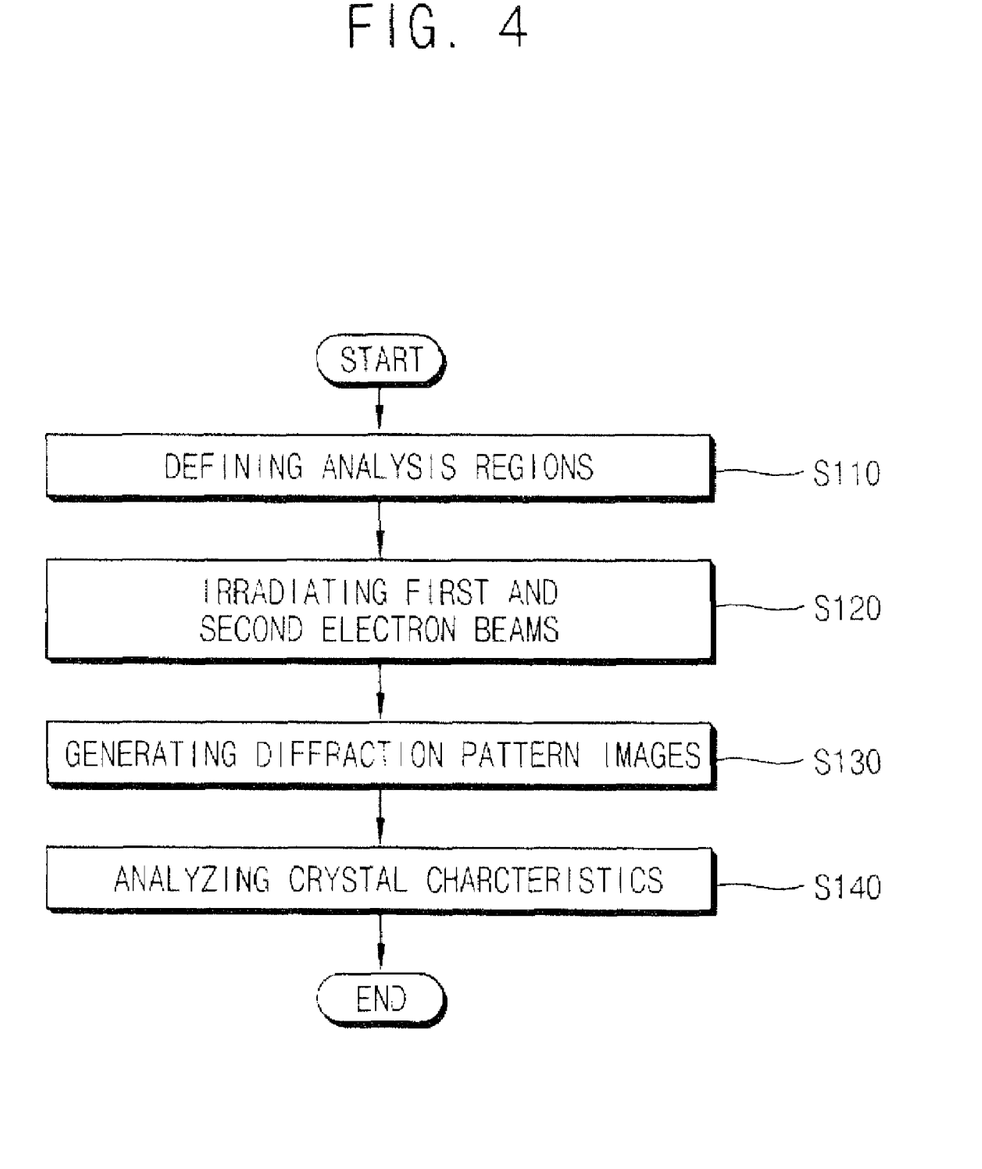
FIG. 4 is a flow chart showing a method of analyzing crystal characteristics in accordance with an example embodiment.

FIG. 4 is a flow chart showing a method of analyzing crystal characteristics in accordance with an example embodiment of the present invention.

Referring to FIGS. 1 and 4, a substrate 200 is loaded onto a stage 130 in a chamber 134, and may be located at a correct position in accordance with overlay marks, for example.

Then, a first electron beam 116 is irradiated from a first beam source 110 onto the substrate 200 that may move in a given direction. In this way, the substrate 200 is scanned by the first electron beam 116.

Image information on circuit patterns of the substrate 200 may be generated while scanning the substrate 200 by the first electron beam 116. Particularly, when the first electron beam 116 is irradiated onto the substrate 200, a plurality of secondary electrons 170 is emitted from the substrate 200. A first detector 142 of a setting unit 140 detects the secondary electrons 170 emitted from the substrate 200, subsequently generating a corresponding electric current. The first detector 142 may also convert the electric current into a corresponding voltage, which is sufficiently amplified in the first detector 142. The amplified voltage signal may be converted into image information on the circuit patterns of the substrate 200 in a first image generator 144.

An analysis region 210 in FIG. 2A of the substrate 200 may be defined on a basis of the image information of the circuit pattern in a first image processor 146 in step S110. An analysis process for analyzing crystal characteristics may be performed in the analysis region on the substrate 200.

Then, a successive irradiation of first and second electron beams may be performed on the analysis region in step S120. The method of scanning the substrate 200 using the first and the second electron beams may be substantially identical to a method of scanning a substrate in accordance with an example embodiment illustrated in FIGS. 2A to 2D or a method of scanning a substrate in accordance with another example embodiment illustrated in FIGS. 3A to 3D. Thus, any further explanations thereof will be omitted.

A spot size of the first and the second electron beams 116 and 126 may be adjusted in accordance with a resolution of the analysis process. When a low resolution is preferred in the analysis process, the substrate 200 may be scanned by the first and second electron beams 116 and 126 having a large spot size as described in the first example embodiment with reference to FIGS. 2A to 2D. For example, the scanning method described in FIGS. 2A to 2D may be performed when a size of the crystal in a circuit pattern is about several tens of nanometers.

When a high resolution is preferred in the analysis process, the substrate 200 may be scanned by the first and the second electron beams 116 and 126 having a small spot size as described in the second example embodiment with reference to FIGS. 3A to 3D. For example, the scanning method described in FIGS. 3A to 3D may be performed when a size of the crystal in a circuit pattern is about a few nanometers.

Whenever the first electron beam 116 is irradiated onto the scanning areas of the substrate, back-scattered electrons and secondary electrons are emitted from the scanning areas of the substrate. Then, the back-scattered electrons may only be detected by the second detector 152, and a linear diffraction pattern, i.e., a Kicuchi image, is generated in the second image generator 154 in accordance with a crystal direction on a theoretical basis of a Bragg diffraction of the detected back-scattered electrons in step S130.

The crystal characteristics of the circuit pattern are analyzed using the diffraction pattern in step S140. For example, a crystal direction of the circuit pattern may be analyzed by the above scanning method.

According to the method of analyzing the crystal characteristics in the present embodiment, the first electron beam 116 is irradiated in a pulse form to decrease an amount of accumulated electrons generated by the first electron beam 116. After the second electron beam 126 discharges the accumulated electrons generated by the first electron beam 116, the first electron beam 116 is irradiated again, thereby preventing the influence of the accumulated electrons. Because the crystals in the patterns of the substrate 200 have a nanoscale in a range of a few nanometers to several tens of nanometers, the crystal characteristics may be easily and clearly analyzed.

According to embodiments, a first electron beam is irradiated in a pulse form so that a reduced amount of charge is accumulated in a substrate. Further, a second electron beam removes the accumulated electrons by the first electron beam from the substrate. As a result, crystal characteristics of the circuit pattern on the substrate are easily analyzed without noises due to the accumulated electrons, although the circuit pattern becomes much finer.

The foregoing is illustrative of some embodiments of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein,

What is claimed is:

1. A method of scanning a substrate, the method comprising:

irradiating a first electron beam onto a first scan area of the substrate resulting in an accumulation of charge on the first scan area, wherein the first electron beam is discontinuously irradiated onto the substrate in a pulse form and the first electron beam is incident at a slope with respect to a surface of the substrate;

irradiating a second electron beam onto the first scan area of the substrate, so that the accumulation of charge on the substrate is discharged from the first scan area by the second electron beam;

irradiating the first electron beam onto a second scan area of the substrate resulting in an accumulation of charge on the second scan area;

irradiating the second electron beam onto the second scan area of the substrate, so that the accumulation of charge on the substrate is discharged from the second scan area by the second electron beam; and repeatedly performing a sequential irradiation of the first and second electron beams onto other scan areas of the substrate.

2. The method of claim 1, wherein the first and second scan areas of the substrate each are larger than a spot size of the first electron beam and are adjacent to each other.

3. The method of claim 1, wherein, the first and second areas of the substrate have a size that is substantially identical to a spot size of the first electron beam and partially overlap each other.

4. The method of claim 1, wherein the slope is from about 20° to 30° from the surface of the substrate.

5. The method of claim 1, wherein the second electron beam is perpendicularly incident to the surface of the substrate.

6. The method of claim 1, wherein the second electron beam has a charge polarity that is the same as the accumulated charge on the substrate so that a charge of the second electron beam collides with the accumulated charge on the substrate caused by the first electron beam so that the first scan area is discharged by the second electron beam.

7. The method of claim 1, wherein the second electron beam has a charge polarity that is opposite to the accumulated charge on the substrate so that the accumulated charge on the substrate caused by the first electron beam is neutralized by a charge of the second electron beam so that the first scan area is discharged by the second electron beam.

8. The method of claim 1, wherein the second scan area does not overlap the first scan area.

9. The method of claim 1, wherein the second scan area partially overlaps the first scan area.

10. The method of claim 9, wherein a spot size of the first electron beam is substantially the same as the first scan area of the substrate.

11. A method of analyzing crystal characteristics of a substrate, the method comprising:
defining a plurality of scan areas on a substrate;
repeating a sequential scanning of each of the scan areas using a first electron beam and a second electron beam, wherein the first electron beam is pulsed and the first electron beam is incident at a slope with respect to the scan areas, so that electrons accumulated in the scan areas by the first electron beam are removed from the scan areas by the second electron beam;
generating diffraction patterns for each of the scan areas using back-scattered electrons emitted from each of the scan areas by irradiating the first electron beam; and
analyzing crystals of a circuit pattern on the substrate using the diffraction patterns.

12. The method of claim 11, wherein each of the scan areas is larger than a spot size of the first electron beam and does not overlap any neighboring scan areas.

13. The method of claim 11, wherein the scan areas have substantially the same size as a spot size of the first electron beam and each of the scan areas partially overlaps neighboring scan areas.

14. The method of claim 11, wherein prior to defining the scan areas, further comprising defining an analysis region including the scan areas on the substrate.

15. The method of claim 14, wherein defining the analysis region on the substrate comprises:
irradiating a third electron beam onto the substrate;
generating pattern images of the substrate using secondary electrons emitted from the substrate; and
defining the analysis region on the substrate using the pattern images.

16. An apparatus for analyzing crystal characteristics, comprising:
a stage supporting a substrate;
a first beam source irradiating a first electron beam to the substrate, wherein the first beam source is arranged to emit a pulsed first electron beam to the substrate and the first beam source is disposed to irradiate the substrate at an angle;
a second beam source adapted to irradiate a second electron beam to the substrate so that electrons accumulated in the substrate by the first electron beam are removed from the substrate;
a first detector detecting secondary electrons emitted from the substrate by irradiating the first electron beam;
a first image generator generating circuit pattern images of the substrate using the detected secondary electrons;
a first image processor defining an analysis region on the substrate using the circuit pattern images;
a second detector detecting back-scattered electrons emitted from the substrate by irradiating the first electron beam;
a second image generator generating diffraction pattern images using the detected back-scattered electrons; and
a second image processor analyzing crystal characteristics of a circuit pattern using the diffraction pattern images.

17. The apparatus of claim 16, wherein the angle is between about 20° to 30°.

18. The apparatus of claim 16, wherein the second beam source is arranged to emit a second electron beam of a same polarity as a charge accumulated on a first scan area of the substrate so that a charge of the second electron beam collides with the accumulated charge on the substrate caused by the first electron beam so that the first scan area is discharged by the second electron beam.

19. The apparatus of claim 16, wherein the second beam source is arranged to emit a second electron beam of an opposite polarity as a charge accumulated on a first scan area of the substrate so that the accumulated charge on the substrate caused by the first electron beam is neutralized by a charge of the second electron beam so that the first scan area is discharged by the second electron beam.

* * * * *